(12) United States Patent
Gu et al.

(10) Patent No.: US 10,182,728 B2
(45) Date of Patent: Jan. 22, 2019

(54) MULTI-SENSOR DEVICE AND METHOD OF USING MULTI-SENSOR DEVICE FOR DETERMINING BIOMETRIC PROPERTIES OF A SUBJECT

(71) Applicant: QUALCOMM Incorporated, San Diego, CA (US)

(72) Inventors: Shiqun Gu, San Diego, CA (US); David Boettcher Baek, San Diego, CA (US); Eugene Dantsker, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 223 days.

(21) Appl. No.: 15/189,089

(22) Filed: Jun. 22, 2016

(65) Prior Publication Data
US 2017/0367594 A1   Dec. 28, 2017

(51) Int. Cl.
*A61B 5/02* (2006.01)
*A61B 5/0205* (2006.01)
*A61B 5/00* (2006.01)
*A61B 5/01* (2006.01)
(Continued)

(52) U.S. Cl.
CPC ........ *A61B 5/02055* (2013.01); *A61B 5/0059* (2013.01); *A61B 5/01* (2013.01); *A61B 5/021* (2013.01); *A61B 5/024* (2013.01); *A61B 5/02007* (2013.01); *A61B 5/0402* (2013.01); *A61B 5/0476* (2013.01);
(Continued)

(58) Field of Classification Search
CPC ... A61B 5/02055; A61B 5/0402; A61B 5/053; A61B 5/024; A61B 5/021; A61B 5/02007; A61B 5/7207; A61B 5/6831; A61B 5/01; A61B 5/6824; A61B 5/0059; A61B 5/0476; A61B 5/0488; A61B 8/13; A61B 5/728
See application file for complete search history.

(56) References Cited

U.S. PATENT DOCUMENTS 8,602,997 B2   12/2013   Banet et al.
8,886,334 B2   11/2014   Ghaffari et al.
(Continued)

FOREIGN PATENT DOCUMENTS

WO   2015165785 A1   11/2015

OTHER PUBLICATIONS

International Search Report and Written Opinion—PCT/US2017/034158—ISA/EPO—dated Aug. 25, 2017.
(Continued)

*Primary Examiner* — Rex R Holmes
(74) *Attorney, Agent, or Firm* — Bala Ramasamy; Kilpatrick Townsend & Stockton

(57) ABSTRACT

Methods, devices, systems, and non-transitory processor-readable storage media are disclosed for determining one or more biometric properties of a subject using multiple sensors positioned along a flexible backing. At least one processor of the multi-sensor device may be configured to receive output signals from the multiple sensors, identify at least one output signal from the received output signals that exhibit measurements of a targeted biological structure, determine the one or more biometric properties of the subject based on the identified at least one output signal received from at least one of the multiple sensors, and provide the determined one or more biometric properties.

33 Claims, 5 Drawing Sheets

(51) Int. Cl.
  *A61B 5/0402* (2006.01)
  *A61B 5/0476* (2006.01)
  *A61B 5/0488* (2006.01)
  *A61B 8/13* (2006.01)
  *A61B 5/021* (2006.01)
  *A61B 5/024* (2006.01)
  *A61B 5/053* (2006.01)
  *A61B 5/11* (2006.01)

(52) U.S. Cl.
  CPC ............ *A61B 5/0488* (2013.01); *A61B 5/053* (2013.01); *A61B 5/11* (2013.01); *A61B 5/6824* (2013.01); *A61B 5/6831* (2013.01); *A61B 5/7207* (2013.01); *A61B 5/7285* (2013.01); *A61B 8/13* (2013.01); *A61B 2562/0219* (2013.01); *A61B 2562/0247* (2013.01); *A61B 2562/0271* (2013.01); *A61B 2562/164* (2013.01)

(56) References Cited

U.S. PATENT DOCUMENTS

| | | |
|---|---|---|
| 2008/0319327 A1 | 12/2008 | Banet et al. |
| 2011/0184270 A1* | 7/2011 | Russell .............. A61B 5/02055 600/388 |
| 2015/0272458 A1 | 10/2015 | Magniez et al. |
| 2015/0309535 A1 | 10/2015 | Connor et al. |
| 2016/0051193 A1* | 2/2016 | Park ...................... A61B 5/681 600/300 |

OTHER PUBLICATIONS

Bansal A.K., et al., "Wearable Organic Optoelectronic Sensors for Medicine," Communication, 2014, pp. 1-7.

Lochner C.M., et al., "All-organic optoelectronic sensor for pulse oximetry", Nature Communications, Dec. 10, 2014, pp. 1-7.

* cited by examiner

MULTI-SENSOR DEVICE AND METHOD OF USING MULTI-SENSOR DEVICE FOR DETERMINING BIOMETRIC PROPERTIES OF A SUBJECT

BACKGROUND

Biometric properties, such as blood pressure, pulse rate and other cardiovascular properties, may be monitored using one or more of bio-impedance, optical, and ultrasonic sensor techniques. There are a number of challenges associated with the use of such non-invasive devices for monitoring cardiovascular and other biometric properties. Conventional sensors may need to be arranged close to the skin surface to detect targeted biological features and/or properties. For example, optical sensors may penetrate only a few millimeters below the skin, while ultrasonic sensors may penetrate several centimeters below the skin. Such short-range sensors may need to be positioned over or close to a subcutaneous biological structure (e.g., an artery, vein, bone, etc.) to obtain suitable measurements. However, it may be difficult to determine where to position such a conventional sensor on a subject. Some biological structures, such as arteries and muscle tissue, can move around within a volume of tissue, such that the location of the biological structure may change from one measurement to the next, further complicating accurate positioning of short-range biological sensors on a subject.

SUMMARY

Various embodiments include a multi-sensor device and methods of using a multi-sensor device for determining one or more biometric properties of a subject. In some embodiments, the multi-sensor device may be configured to determine biometric properties of the subject such that perfect placement of the device relative to a targeted biological structure (e.g., artery) is not required. In some embodiments, the multi-sensor device may be configured to dynamically correct for any misalignment between the multi-sensor device and a measurement location due to device or patient movements, such that the biometric properties may be determined only from output signals of sensor(s) that exhibit measurements or characteristics of the targeted biological structure.

In various embodiments, the device for determining one or more biometric properties of a subject may include a flexible backing, multiple sensors positioned along the flexible backing, and at least one processor coupled to the multiple sensors. The processor may be configured to receive output signals from the multiple sensors, identify at least one output signal from the received output signals that exhibits measurements of a targeted biological structure, determine the one or more biometric properties of the subject based on the identified output signal received from at least one of the sensors, and provide the determined one or more biometric properties. In some embodiments, the flexible backing may be a flexible strip configured to wrap around a subject or a portion of the subject in a helical manner. In some embodiments, the sensors may be covered with a material to protect the skin.

In some embodiments, to identify the output signal from the received output signals that exhibits measurements of the targeted biological structure, the processor may be further configured to compare the received output signals from the sensors to a reference signal that models the targeted biological structure and identify the output signal based on the comparison.

In some embodiments, the sensors may include one or more types of sensors and the processor may be further configured to activate the one or more types of sensors to obtain different measurements of the targeted biological structure. In some embodiments, the one or more types of sensors may include optical sensors, bio-impedance sensors, ultrasound imagers, ultrasound sensors, pressure sensors, Peltier sensors, electrocardiogram (ECG) sensors, electromyography (EMG) sensors, electroencephalography (EEG) sensors, ultraviolet (UV) sensors, accelerometers, inertia sensors, or any combination thereof.

In some embodiments, the processor may be further configured to change an activation state of one or more of the sensors that is not associated with the identified output signal to a reduced activation state.

In some embodiments, the processor may be configured to activate all of the plurality of sensors simultaneously. In some embodiments, the processor may be configured to activate at least one subset of the sensors at a similar time. In some embodiment, the subset of sensors activated at a similar time may include different types of sensors. In other embodiments, the subset of sensors activated at a similar time may include the same type of sensors. In some embodiments, the processor may be configured to activate the sensors periodically or quasi-periodically to generate the output signals.

In some embodiments, the processor may be further configured to detect a change in the at least one output signal received from the at least one sensor, identify at least one other output signal that exhibit measurements of the targeted biological structure received from at least one different sensor in response to detecting the change in the at least one output signal, and determine the one or more biometric properties of the subject based on the identified at least one output signal received from at least one different sensor.

Further embodiments may include a method for determining one or more biological properties of a subject using a device comprising multiple sensors positioned along a flexible backing, which may include receiving output signals from the sensors, identifying at least one output signal from the received output signals that exhibits measurements of a targeted biological structure, determining the one or more biometric properties of the subject based on the identified output signal received from at least one of the sensors, and providing the determined one or more biometric properties. In some embodiments, identifying the output signal from the received output signals that exhibits measurements of the targeted biological structure may include comparing the received output signals from the sensors to a reference signal that models the targeted biological structure and identifying the output signal based on the comparison.

In some embodiments, the sensors may include one or more types of sensors and the method may further include activating the one or more types of sensors to obtain different measurements of the targeted biological structure. In some embodiments, receiving the output signals from the sensors may include receiving the output signals from optical sensors, bio-impedance sensors, ultrasound imagers, ultrasound sensors, pressure sensors, Peltier sensors, electrocardiogram (ECG) sensors, electromyography (EMG) sensors, electroencephalography (EEG) sensors, ultraviolet (UV) sensors, accelerometers, inertia sensors, or any combination thereof.

In some embodiments, the method may further include changing an activation state of one or more of the sensors that are not associated with the identified at least one output signal to a reduced activation state. In some embodiments, the method may further include activating all of the plurality of sensors simultaneously. In some embodiments, the method may further include activating subsets of the plurality of sensors at a similar time. In some embodiments, the method may further include activating periodically or quasi-periodically the plurality of sensors to generate the output signals.

In some embodiments, the method may further include detecting a change in the output signal received from the at least one sensor, identifying at least one other output signal that exhibits measurements of the targeted biological structure received from at least one different sensor in response to detecting the change in the at least one output signal, and determining the one or more biometric properties of the subject based on the identified at least one output signal received from at least one different sensor.

Further embodiments may include a device for determining one or more biological properties of a subject, which may include a flexible backing, multiple sensors positioned along the flexible backing, and means for performing functions of the operations of the embodiment methods described above.

Further embodiments may include a non-transitory processor readable storage medium having stored thereon processor executable instructions configured to cause a processor of a multi-sensor device that may include multiple sensors positioned along a flexible backing to perform operations, which may include receiving output signals from the multiple sensors, identifying at least one output signal from the received output signals that exhibits measurements of a targeted biological structure, determining the one or more biometric properties of a subject based on the identified output signal received from at least one of the sensors, and providing the determined one or more biometric properties.

BRIEF DESCRIPTION OF THE DRAWING

The accompanying drawings, which are incorporated herein and constitute part of this specification, illustrate example embodiments of the claims, and together with the general description given above and the detailed description given below, serve to explain the features of the claims.

DETAILED DESCRIPTION

Figure 1:
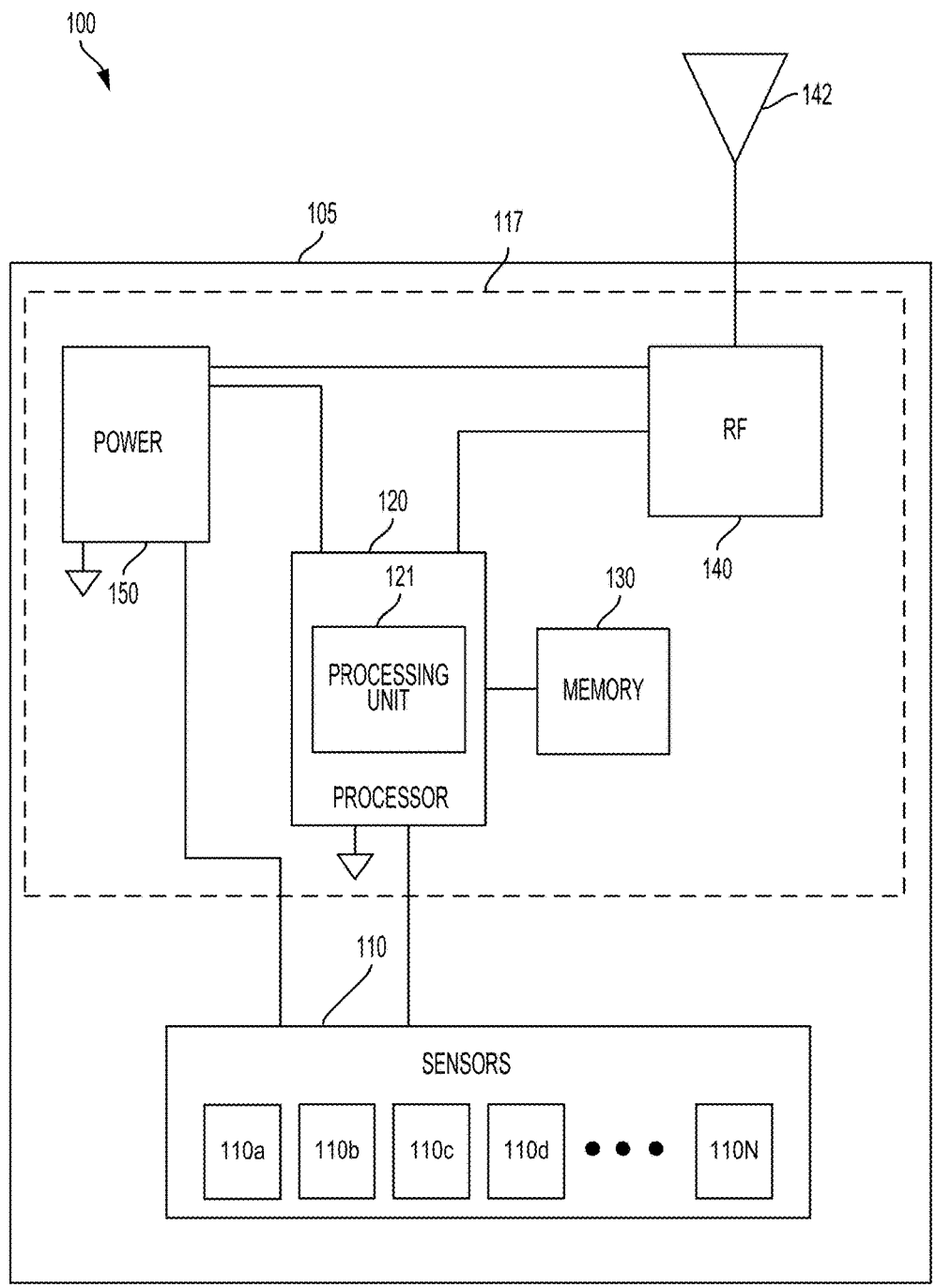
FIG. 1 is a schematic diagram illustrating example components of a multi-sensor device for determining biometric properties of a subject according to some embodiments.

Various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the claims.

The term "biometric properties" is used herein as a general term to refer to characteristics of a biological system of a human subject, including but not limited to cardiovascular properties of a cardiovascular system. Examples of cardiovascular properties may include, but are not limited to, arterial beat-to-beat distension, pulse rate, pulse transit time (PTT), pulse wave velocity (PWV), arterial cross-sectional area, arterial stiffness, heart rate, heart rate variability, and blood pressure. Further examples of a biometric property may include muscle activity.

The term "limb" is used herein to refer to a finger, wrist, forearm, ankle, leg, or other body part suitable for taking measurements of a targeted biological structure.

The term "quasi-periodic" is used herein to refer to an event that occurs periodically with a frequency that may change from time to time, and/or to an event that occurs from time to time with no well-defined frequency.

Various embodiments include a multi-sensor device and a method of using a multi-sensor device for determining one or more biometric properties of a subject. In some embodiments, the multi-sensor device may be configured to determine biometric properties of the subject such that perfect placement of the device relative to a targeted biological structure (e.g., an artery) is not required. In some embodiments, the multi-sensor device may be configured to dynamically correct for any misalignment between the multi-sensor device and a measurement location due to device or patient movements. In some embodiments, the biometric properties may be determined only from output signals of sensor(s) that exhibit measurements or characteristics of the targeted biological structure.

In some embodiments, the multi-sensor device may be configured for use in scanning a limb or other body part to search for and obtain biometric measurements of targeted biological structures, such as arteries, veins, bones, and other biological tissue for example. In some embodiments, the multi-sensor device may include multiple sensors arranged in a series, array, matrix, random, or other pattern along the length of the flexible sensor strip. A multi-sensor device according to some embodiments may be placed in direct contact with a skin surface of a subject, such as along or around a limb of the subject. In some embodiments, the sensors may be in contact with the skin indirectly, such as via sweat, a conductive gel, air gap, etc. In some embodiments, the multi-sensor device may be configured so that it can be helically wrapped around a limb, thereby contacting the limb both radially and along a length.

In some embodiments, the sensors of the multi-sensor device may be activated simultaneously, individually, or in various groups to detect and generate output signals corresponding to measurements of various biological features or properties of underlying tissues. The sensors may include short-range sensors that provide measurements when positioned over or near a particular type ("targeted") of biological structure, such an artery, vein, tendon, muscle, bone, or any combination thereof. Including multiple sensors arranged along the multi-sensor device may simplify placement on a subject as the number of sensors increases the chances of properly placing one or more of the sensors with respect to a targeted biological structure.

In some embodiments, the sensors arranged along the multi-sensor device may include one or more of optical sensors, bio-impedance sensors, ultrasound sensors, and pressure sensors, Peltier sensors, electrocardiogram (ECG) sensors, electromyography (EMG) sensors, electroencephalography (EEG) sensors, ultraviolet (UV) sensors, accelerometers, inertia sensors, or any combination thereof. In some embodiments, the sensors arranged on the flexible sensor strip 100 may be covered with a foam, non-wove, rubber or other material to protect the skin.

In some embodiments, the output signals generated by the sensors may be analysed by a processor to identify the information in the signals that corresponds to the targeted biological structure. The processor may then process the identified output signal(s) to obtain or calculate measurements of a desired medical or biometric property. Optionally, the processor may change the activation state of one or more sensors that are not exhibiting measurements corresponding to the targeted biological structure to a reduced activation state, thereby conserving power and/or reducing energy emitted into the subject (e.g., the electrical signals applied to skin by bio-impedance sensors). For example, sensors in a reduced activation state may be deactivated or activated at a reduced rate. For example, sensors exhibiting measurements that indicate the sensors are not close to a targeted artery may perform measurements every few minutes, while a sensor exhibiting measurements that indicate the sensor is close enough to the artery to obtain reliable measurements may be activated to perform measurements every second.

FIG. 1 is a schematic diagram illustrating example components of a multi-sensor device for determining biometric properties of a subject according to some embodiments. A multi-sensor device 100 may include a pattern of multiple sensors 110a-110N within a sensor array 110, a processor 120, memory 130, a radio frequency (RF) resource 140 coupled to an antenna 142, and a power supply 150 arranged on a flexible backing 105. In some embodiments, the multi-sensor device 100 may have a semi-flexible backing. In some embodiments, the multi-sensor device 100 may have a rigid backing.

In some embodiments, the flexible backing 105 may be implemented with flexible materials so that the multi-sensor device 100 may wrap around or otherwise conform to the surface of the subject, such as a limb or other body part. In some embodiments, the flexible backing 105 may be configured to roll up into a coil for storage purposes.

In some embodiments, the sensors 110a-110N of the multi-sensor device 100 may be arranged and positioned to be in direct contact with a subject's skin when applied to the subject. In some embodiments, the sensors 110a-110N may be in contact with the subject's skin indirectly such as via sweat, a conductive gel, air gap, etc.

In some embodiments, the multi-sensor device 100 may be configured in the form of, or incorporated into, a free form flexible strip, a spring-biased strip (biased to roll), a finger sleeve, a wrist cuff, band of a wrist watch, a waist band or belt, a head band, and/or other form of strip or apparel (e.g., clothing that includes an embodiments of the multi-sensor device 100). However, the various embodiments are not limited to implementations that are directly worn by a subject, and may include other types of configurations that may place the sensors 110a-110N against the skin of the subject. For example, in some embodiments, the multi-sensor device 100 may be incorporated into safety belts, steering wheels, armrests, seats and other structures in an automobile, train, airplane, or other vehicle, and configured so that the sensors 110a-110N may come into contact with the skin of a subject. In another example, the multi-sensor device 100 may be incorporated into smart furniture and configured so that the sensors 110a-110N come in contact with the skin of a subject. As a further example, in some embodiments, the multi-sensor device 100 may be incorporated into athletic equipment, such as helmets, racket handles, wrist or headbands, shoes, socks, handle bars, etc., and configured so that the sensors 110a-110N may come into contact with the skin of a subject.

The multi-sensor device 100 may include any number of sensors 110a-110N arranged along the length of the flexible backing 105. In some embodiments, the number of sensors 110a-110N and the corresponding length of the multi-sensor device 100 may be configured for scanning a particular limb or other body part. For example, the multi-sensor device 100 may be configured with a few sensors and corresponding length for scanning a finger (e.g., a flexible strip sized for use on fingers), and several sensor for scanning a forearm or leg (e.g., a flexible strip sized for use on major limbs). In some embodiments, the number of sensors 110a-110N and the corresponding length of the multi-sensor device 100 may be configured to include a number of sensors arranged along the length of the flexible backing that is sufficient to scan across a limb for which the multi-sensor device is configured (e.g., a finger strip vs. a major limb strip).

In some embodiments, the multi-sensor device 100 may be configured to determine which of the sensors 110a-110N will be activated and used based on the limb or other body part to be scanned, a length of the multi-sensor device employed, or any overlap of the sensors when applied to a subject.

In some embodiments, one or more of the sensors 110a-110N may have a flexible structure so that the sensors may conform to the shape of the limb. In some embodiments, the sensors 110a-110N may have a rigid structure. In some embodiments, the sensors 110a-110N may have a structure that includes both flexible components and rigid components.

In some embodiments, each of the sensors 110a-110N may be configured to detect phenomenon and generate output signals that represent, or correspond to, a response from biological tissue within the limb to an input signal applied by the respective sensors to the limb. For example, in some embodiments, the input signal may be electrical potential, current, light, ultrasound, or any combination thereof.

In some embodiments, the sensors 110a-110N may include one or more bio-impedance sensors, each configured to detect and generate output signals in which the amplitude of the signals represent a voltage response of biological tissue to an applied current or voltage potential. In some embodiments, the bio-impedance sensors may be configured as pairs of electrodes that measure impedance through tissues of electrical signals (such as an alternating current with a high frequency or a voltage potential) applied across the electrodes. For example, each bio-impedance sensor may be configured as a pair of pickup electrodes and an adjacent pair of injection electrodes so that the voltage response may be detected in response to applied current or voltage potential injected across a localized volume of the limb.

In some embodiments, a pair of injection electrodes may be arranged towards the terminal ends of the multi-sensor device 100. In some embodiments, the injection electrodes may be placed away from the terminal ends of the sensors strip. In some embodiments, the injection electrodes may be applied to the subject's limb or other body part separate and apart from the multi-sensor device 100. In some embodiments, the pickup electrodes and the injection electrodes may be arranged in the multi-sensor device 100 in a series or parallel arrangement. In some embodiments, each electrode may be operated as an injection electrode or a pickup electrode due to the principle of reciprocity in bio-impedance measurements (e.g., the injection electrodes and pickup electrodes may be swapped). In some embodiments, each electrode may be operated as both an injection electrode and a pickup electrode.

The voltage response detected by a bio-impedance sensor may depend on the conductivity and permittivity of the biological tissue falling within the field of view of the pickup electrodes. For example, when an artery is within the field of view, the pickup electrodes of a bio-impedance sensor may generate an amplitude modulated signal that correlates to the distension of the artery with each heartbeat. The amplitude modulation may vary and depend on how much of the artery falls between the set of pick-up electrodes and the angle between the electrical field lines caused by the injected current.

In some embodiments, where a voltage potential is applied by the injection electrodes, the bio-impedance sensors may be configured in the form of a Kelvin probe, which may eliminate problems with high impedance traces in certain bandwidths.

In some embodiments, the sensors 110a-110N may include one or more optical sensors, each configured to detect and generate output signals in which the amplitude of the signals represent the intensity of light reflected (or backscattered) by biological tissue within the sensor's field of view. For example, when an artery is located below an optical sensor, the sensor may generate an amplitude modulated signal in which the intensity of the reflected light correlates with the arterial distension of a heartbeat. The optical sensors may each include a light emitter and light detector also called a photo detector. In some embodiments, the light emitter may be configured as an organic light emitting diode (OLED) and the light detector may be configured as an organic photodiode detector (OPD).

In some embodiments, the sensors 110a-110N may include one or more ultrasonic sensors, each configured to detect and generate output signals that represent reflected ultrasound when the ultrasonic sensor injects ultrasound into the subject's limb. For example, in some embodiments, each ultrasonic sensor may be configured as an ultrasonic transmitter and receiver. In some embodiments, the ultrasonic receivers may be configured to generate an output signal that corresponds to an RF voltage response having a time length corresponding to the ultrasonic wave's travel time into the tissue and back from a reflection point. Because blood does not reflect ultrasound as much as the arterial wall and surrounding tissues, an ultrasonic sensor located directly above an artery may generate a low amplitude output signal for the part of the signal corresponding to the artery depth.

In some embodiments, the sensors 110a-110N may include one or more Peltier sensors, which could be used for cooling or heating locally. In some embodiments, the sensors 110a-110N may include one or more electromyography (EMG) sensors configured for monitoring muscle activity. In some embodiments, the sensors 110a-110N may include one or more electroencephalography (EEG) sensors configured to monitor electrical activity of the brain. In some embodiments, the sensors 110a-110N may include one or more electrocardiogram (ECG) sensors configured to monitor electrical activity of the heart.

In some embodiments, the sensors 110a-110N may include one or more accelerometers or inertia sensors configured to monitor the motion of a limb or other body part. For example, by including multiple accelerometers or inertia sensors in the multi-sensor device 100 and wrapping the device around the lower and upper arm, for example, the motion of the arm may be observed for the purpose of optimizing the subject's abilities in certain sports (e.g., golf swing, pitching, etc.).

In some embodiments, the sensors 110a-110N may include one or more ultraviolet (UV) sensors configured to determine the vein pattern of a subject. For example, vein patterns are generally unique from person to person and, thus, may be used for identification purposes. When the UV sensor illuminates vein blood with UV light, the UV light reflected by the vein blood may be used to determine the subject's vein pattern.

In some embodiments, the sensors 110a-110N may also include one or more pressure sensors configured to monitor blood pressure if an inflating counter pressure is applied.

In some embodiments, the sensors 110a-110N may include multiple sensors of the same type. For example, sensors of the same type (e.g., optical, bio-impedance, or ultrasound, etc.) may be arranged in a pattern along the length of the multi-sensor device 100. In some embodiments, the sensors 110a-110N arranged along the flexible backing 105 may include a combination of different types of sensors. For example, the multi-sensor device 100 may be configured with a set of optical sensors in combination with a set of bio-impedance sensors.

In some embodiments, each of the sensors 110a-110N may be individually coupled to the processor 120 so that the processor may control or receive outputs from each sensor. In some embodiments, the processor 120 may be dedicated hardware specifically adapted to perform a variety of functions of the flexible sensor strip 100. In some embodiments, the processor 120 may be or include a programmable processing unit 121 that may be programmed with processor-executable instructions. In some embodiments, the processing unit 121 may be a programmable microprocessor, microcomputer or multiple processor chip or chips that can be configured by software instructions to perform a variety of functions for the multi-sensor device 100. In some embodiments, the processor 120 may be a combination of dedicated hardware and a programmable processing unit 121.

In some embodiments, the memory 130 may store processor-executable instructions and/or outputs from the sensors 110a-110N. In some embodiments, the memory 130 may be volatile memory, non-volatile memory (e.g., flash memory), or a combination thereof. In some embodiments, the memory 130 may include internal memory included in the processor 120, memory external to the processor 120, or a combination thereof.

In some embodiments, the processor 120 may be configured to selectively control when the sensors 110a-110N are activated and deactivated (e.g., turned on and off). For example, the processor 120 may be configured to activate the sensors 110a-110N simultaneously, sequentially, individually, or in various groups. Also, the processor 120 may be configured to receive signal from the sensors 110a-110N simultaneously, sequentially, individually, or in various groups.

In some embodiments, the processor 120 may be configured to process output signals received from the sensors 110a-110N to determine the output signals that exhibit characteristics indicating that a targeted biological structure is being measured or sensed. For example, when the targeted biological structure is an artery, the processor 120 may be configured to process the output signals from the sensors 110a-110N in order to identify one or more output signals consistent with pulses within an artery. In this manner, the processor 120 may select one or a few sensors that are well positioned on the subject (e.g., over an artery) to monitor and process output signals from the selected sensors for determining one or more biological measurements. In some embodiments, the processor 120 may be configured to deactivate or transition those sensors that do not produce the identified output signals to a low power mode.

Some biological structures, such as arteries, may shift within tissues due to movements, and the multi-sensor device 100 may shift with respect to the subject. Some embodiments may accommodate this by configuring the processor to continuously, periodically or quasi-periodically activate one or more of the sensors 110a-110N to identify one or more output signals that exhibit measurements of a targeted biological structure in order to detect when there has been a change in output signals exhibiting such measurements. When the processor detects that the output signals exhibiting measurements of a targeted biological structure (i.e., the sensor(s) positioned over the targeted biological structure have changed), the processor may change the sensor(s) or the output signal(s) that are received and/or processed.

In some embodiments, the processor 120 may further process the identified output signal to measure one or more biometric properties of the targeted biological structure. For example, when the targeted biological structure is an artery, the processor 120 may be configured to analyze the output signal and produce a measurement of one or more biometric properties (e.g., cardiovascular properties that may be determined from measurements of an artery).

In some embodiments, the processor 120 may be configured to estimate one or more biometric properties based on the output signals of two or more sensors 110a-110N that correspond to the targeted biological structure. For example, the processor 120 may be configured to measure a pulse transit time (PTT) and pulse wave velocity (PWV) based on the output signals from sensors at the two different locations along the flexible backing 105 of the multi-sensor device 100.

In some embodiments, the processor 120 may be coupled to a radio frequency (RF) resource 140 coupled to an antenna 142 in order to communicate the calculated or measured biometric properties and/or output data from the sensors 110a-110N to a remote computing device (e.g., 250 of FIG. 2) for presentation through a display or other output device. The RF resource 140 may be a transmit-only or a two-way transceiver processor. For example, the RF resource may include base band, intermediate and transmit frequency encoders and decoders. The RF resource 140 may operate in one or more of a number of radio frequency bands depending on the supported type of communications. In some embodiments, a wired network connection (e.g., a Universal Serial Bus (USB) port) (not shown) may be included in place of or in addition to an RF resource 140 to enable passing sensor data or measurements to a remote computing device.

The processor 120 may be configured to transmit measured or calculated information, such as values of the biometric properties or the output from the sensors 110a-110N, to a remote computing device 250 (FIG. 2) for recording or display. Such a remote computing device may be any of a variety of computing devices, including but not limited to a processor in smart clothing, cellular telephones, smart-phones, web-pads, tablet computers, Internet enabled cellular telephones, wireless local area network (WLAN) enabled electronic devices, laptop computers, dedicated healthcare electronic devices, personal computers, and similar electronic devices equipped with at least a processor and a communication resource to communicate with the RF resource 140. Measured and/or calculated information may be transmitted from the multi-sensor device 100 to a remote computing device over a wireless link using Bluetooth®, Wi-Fi® or other wireless communication protocol.

The sensors 110a-110N, the processor 120, the memory 130, the RF resource 140, and any other electronic components of the multi-sensor device 100 may be powered by a power supply 150. The power supply 150 may be a battery, a solar cell, or other energy harvesting power supply.

In some embodiments, the sensors 110a-110N may be positioned along the multi-sensor device 100 while the processor 120, the memory 130, the RF resource 140 and power source 150 may be assembled within a package or housing 117. The housing 117, the processor 120 and/or power supply 150 may be coupled to the sensors 110a-110N through a set of conductive traces or wires (not shown) printed on or embedded in the multi-sensor device 100.

Figure 2:
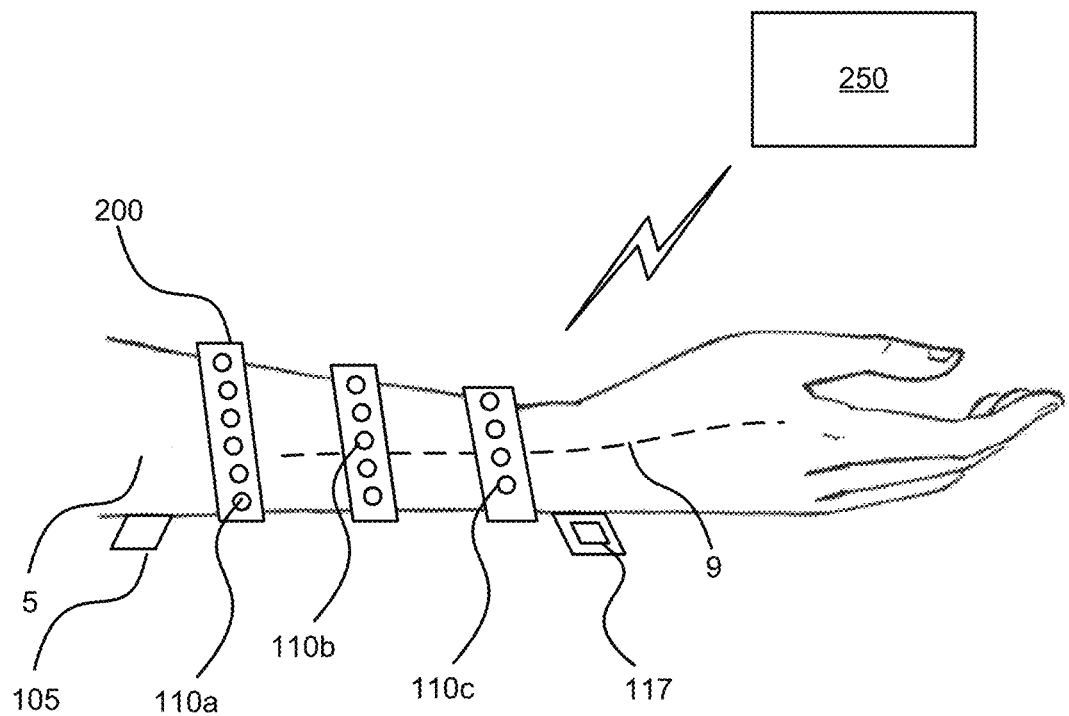
FIG. 2 illustrates a multi-sensor device for determining biometric properties of a subject according to some embodiments.

FIG. 2 illustrates a multi-sensor device for determining biometric properties of a subject according to some embodiments. As illustrated, the multi-sensor device 100 may be configured in the form of a flexible sensor strip 200. In some embodiments, the flexible sensor strip 200 may be helically wrapped around the subject's arm or other limb to scan a measurement volume that extends along the length of the arm or limb. The measurement volume may be scanned for sensor signals exhibiting measurements of an artery 9 or other targeted biological structures, such as veins, bones, or other biological tissues.

As shown in FIG. 2, the flexible sensor strip 200 may be helically wrapped around the subject's arm from the forearm to the wrist. In some embodiments, the flexible sensor strip 200 may include some rigid portions, such as a rigid terminal end. For example, the flexible sensor strip 200 may include one or more rigid terminal ends, which may include the housing 117 in which are positioned the processor 120, the memory 130, the RF resource 140, the antenna 142, and/or the power supply 150 (FIG. 1).

In some embodiments, the flexible backing 105 of the flexible sensor strip 200 may be configured of a flexible material such as a polymer, plastic or fabric. For example, the flexible material may be a bio-compatible polymer that may be placed in contact with the skin without producing a rash. In some embodiments, the flexible sensor strip 200 may include a cover or other intermediate layer that may prevent direct contact between the polymer and the skin. In some embodiments, the cover layer may include a layer of foam, rubber, non-woven fabric, or any combination thereof. In some embodiments, the cover layer may define holes or openings in the cover layer that expose the respective sensors. In some embodiments, the flexible sensor strip 200 may be assembled from a series of metallic or plastic links.

In other embodiments, the flexible sensor strip 200 may be integrated into a form of apparel (i.e., clothing that includes an embodiment of the flexible sensor strip 200), such that the flexible sensor strip 200 may wrap around a subject's limb in a helical manner when worn. For example, the flexible sensor strip 200 may be lined along a sleeve of a shirt or jacket or along a pant leg. However, the various embodiments are not limited to implementations that are directly worn by a subject, and may include configurations that place the sensors 110a-110N in direct or indirect contact with the skin of the subject. For example, the flexible sensor strip 200 may be incorporated into safety belts, steering wheels, armrests, seats and other structures in an automobile, train, airplane, or other vehicle, and configured so that the sensors 110a-110N may come in contact with the skin of a subject at measurement location. In another example, the flexible sensor strip 200 may be incorporated into smart furniture and configured so that the sensors 110a-110N may come in contact with the skin of a subject at measurement location. In other examples, the flexible sensor strip 200 may be incorporated into athletic equipment, such as helmets, racket handles, wrist or headbands, shoes, socks, handle bars, etc., and configured so that the sensors 110a-110N may come in contact the skin of a subject at measurement location(s).

In some embodiment, the flexible sensor strip 200 may come in any physical form. For example, it may be a patch, circle, etc. Additionally, it may be any type of wearable device, such as a shirt, shoes, socks, watches, jewelry, etc.

Figure 3:
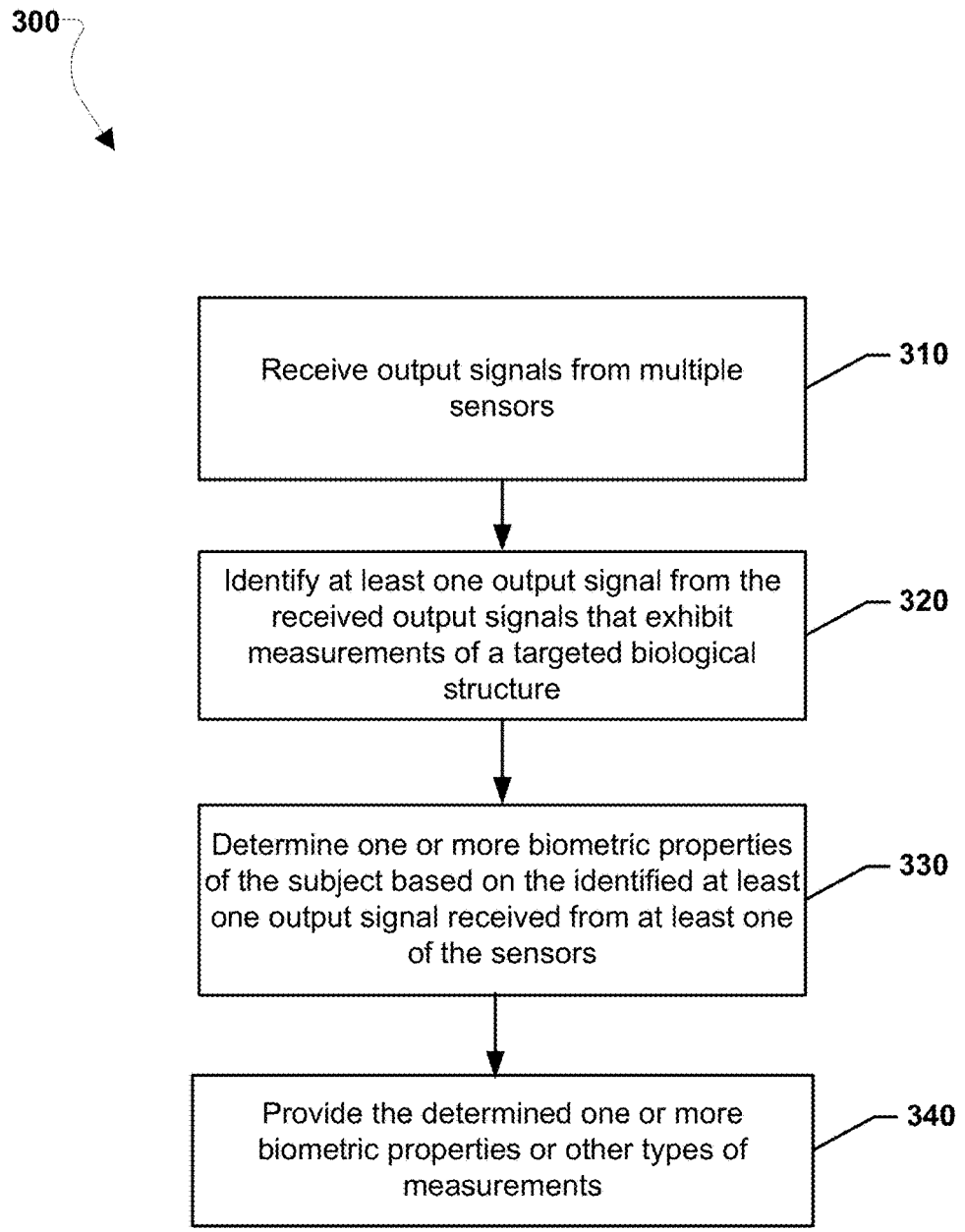
FIG. 3 is a process flow diagram illustrating a method for determining one or more biological properties of a subject using a multi-sensor device according to some embodiments.

FIG. 3 is a process flow diagram illustrating a method 300 for determining one or more biological properties of a subject using a multi-sensor device 100 according to some embodiments. In some embodiments, the targeted biological structure may be an artery, a vein, a bone, other biological structure or any combination thereof that can be measured or sensed in order to determine a desired biological property, such as blood pressure, pulse rate, etc.

In block 310, the processor 120 may receive the output signals generated by the sensors 110a-110N. When a sensor is activated, the sensor may generate an output signal that corresponds to a detected response to a physical stimulus directed into the limb. For example, in some embodiments, the physical stimulus may be electrical current, light, or ultrasound. In some embodiments, the sensors 110a-110N may include different types of sensors (e.g., optical, ultrasonic, bioimpedance, etc.), such that sensors of each type may be activated by the processor 120 to obtain different measurements of the targeted biological structure.

In some embodiments, the processor 120 may be configured to activate the sensors 110a-110N simultaneously or individually, or in groups. In some embodiments, the processor 120 may be configured to activate a subset of the same type of sensors at a similar time (i.e., at the same time or within a short duration of time, e.g., within seconds). For example, the processor 120 may be configured to activate one or more of the bioimpedance sensors within a similar time to locate and/or obtain one set of measurements associated with a targeted artery. Subsequently, the processor 120 may activate one or more other sensors of the same type within a similar time (e.g. optical sensors, etc.) to obtain a different set of measurements associated with the targeted artery. In some embodiments, the processor 120 may be configured to activate a subset of different types of sensors to obtain a specific set of measurements of the targeted biological structure. For example, the processor 120 may activate one or more optical sensors and one or more ultrasonic sensors and then choose amongst the output signals received from the different types of sensors to identify at least one output signal that exhibits measurements of the targeted biological structure.

In block 320, the processor 120 may identify at least one output signal from the received output signals that exhibits measurements of a targeted biological structure. For example, where the targeted biological structure is an artery and the output signals are generated by bio-impedance sensors or optical sensors, the processor 120 may be configured to identify one or more output signals that exhibit measurements or characteristics of the artery by comparing the output signals to a reference signal that models an artery, e.g., an arterial pulse, and identifying the one or more output signals based on the comparison. In some embodiments, the processor 120 may apply a correlation function between each output signal and the arterial reference signal in order to compare how well each output signal correlates to the reference signal, and identify the output signal having the strongest correlation value as exhibiting measurements or characteristics of the artery. In some embodiments, the comparison may be based on a correlation of each output signal to the arterial reference signal with respect to one or more of a phase, amplitude, pulse shape, or other measurement or combination of measurements of the targeted artery.

Figure 4:
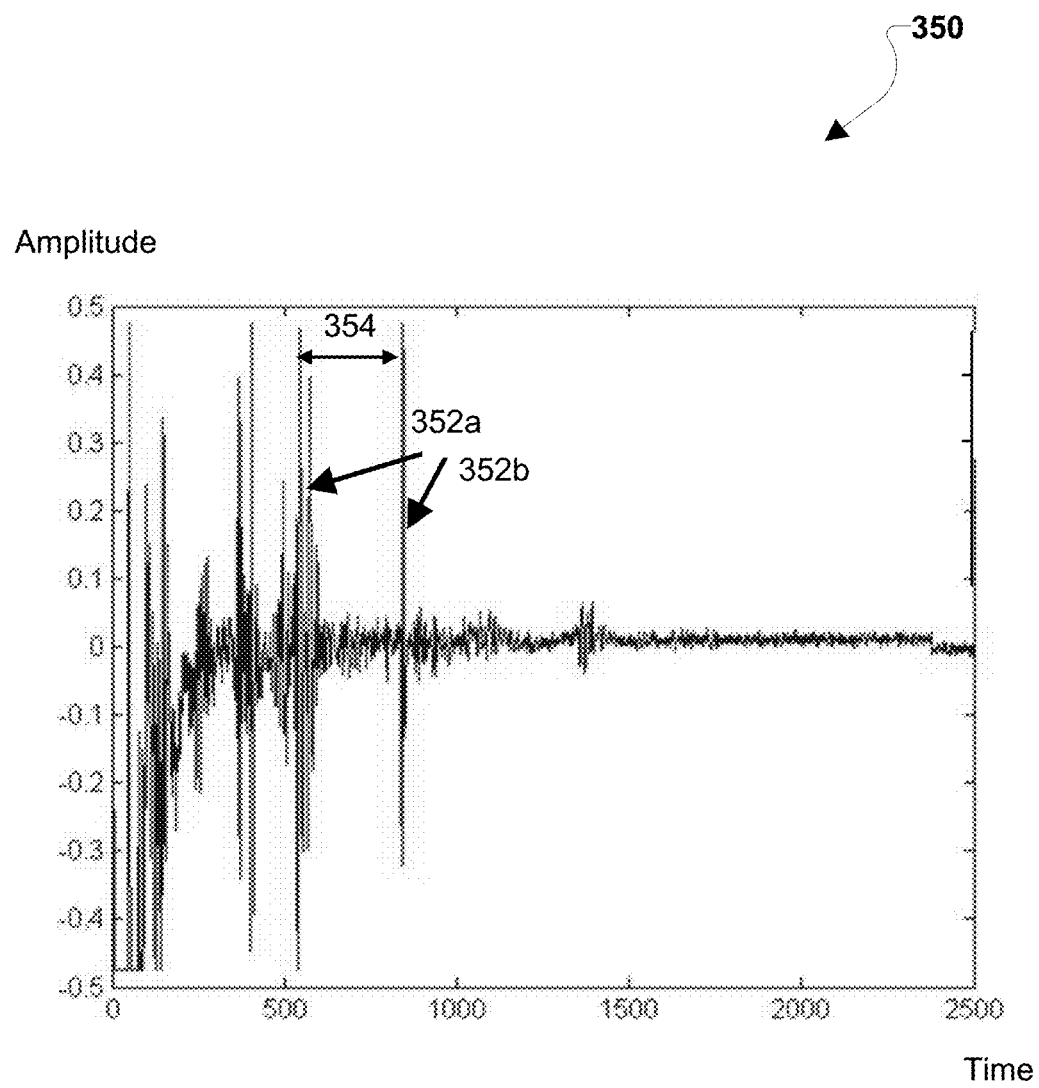
FIG. 4 is a graph that illustrates a phase tracking process to identify an output signal that exhibits measurements or characteristics of an artery using an ultrasonic sensor according to some embodiments.

In some embodiments, where the targeted biological structure is an artery and the output signals are generated by ultrasonic sensors, the processor 120 may be configured to identify one or more output signals that exhibit measurements or characteristics of the artery by the tracking the phase of the output signals received from the sensors 110a-110N. For example, FIG. 4 is a graph 350 that illustrates a phase tracking process to identify an output signal that exhibits measurements or characteristics of an artery using an ultrasonic sensor according to some embodiments. In particular, FIG. 4 illustrates an example of an output signal of an ultrasonic sensor in response to the injection of an ultrasonic beam into the limb of a subject as a function of amplitude over time. As illustrated, when the ultrasonic sensor injects an ultrasonic beam into the limb, the arterial walls will typically generate two dominating spikes 352a, and 352b. These spikes 352a, 352b will ideally be moving away from each other in the systolic phase of a pulse waveform and moving toward each other during the diastolic phase. By tracking the time shift of the spikes 352a, 352b, the processor 120 can calculate how much the artery has expanded based on spike separation 354. In another embodiment, an arterial signal may be identified by tracking the phase of the output signal by observing the phase of a Fourier transformed version of the segments corresponding to the artery wall, and thus observe changes in the phase of the signal that corresponds to the pulsing of the artery.

Returning to FIG. 3, in block 330, the processor 120 may determine one or more biometric properties of the subject based on the one or more output signals received from at least one of the sensors identified in block 320. In some embodiments, the processor 120 may transmit the sensor output to a remote computing device (e.g., 250) to determine the one or more biometric properties based on the output signals identified in block 320. For example, the processor may transmit sensor outputs to a smartphone or other mobile device in a wireless signal (e.g., a Bluetooth® or other wireless local area network (WLAN) signal via an RF resource 140 and an antenna 142.) For example, in implementations in which the targeted biological structure is an artery, the processor 120 or the remote computing device 250 may process the output signal to determine one or more cardiovascular properties, such as arterial distension, cross-sectional area, heart rate, and blood pressure.

Some cardiovascular properties, such as pulse transit time (PTT) and pulse wave velocity (PWV), may use arterial pulse signals from at least two sensors and a value corresponding to the distance propagated along the artery between the two sensor locations. However, in embodiments in which the multi-sensor device 100 is helically wrapped around a limb, the distance may not be determined simply as the distance between the respective sensors 110a-110N within a sensor array 110 on the device 100. For example, where the multi-sensor device is a flexible sensor strip that is helically wrapped around a subject's limb (e.g., 200 of FIG. 2), the distance traveled by a pulse between two sensor locations may be determined based on a parametric representation of a helix. For example, a helix can be parametrically represented as:

$$x = R * \cos[\theta] \quad (1)$$

$$y = R * \sin[\theta] \quad (2)$$

$$z = \text{pitch} * \theta \quad (3)$$

where x, y, and z represent the dimensions of the helix in three-dimensional space, R is the radius of the helix, pitch is a constant determining how quickly the helix will wind up (i.e., the width of one complete turn of the helix measurement parallel to the axis of the helix) and angle θ where θ∈[0, k*2π] of the helix representing the winding location of the given sensor element, k is the number of windings and may be a fractional part, e.g. if the helix has three full windings, then k=3.

In some embodiments, the distance between two of the sensors 110a-110N along the trajectory of a helically wrapped sensor strip 200 may be calculated based on the known relative placement between two sensors on the strip 200 together with the radius R, arc length Arc, and constant pitch. The radius R may be determined by measuring the circumference of the limb to which the flexible sensor strip 200 is applied. The pitch may be calculated based on a measured height of the helix when mounted (i.e., the length of the limb covered by the helically wrapped strip 200) and the overall length of the strip 200. The arc length, Arc, of a helix may be determined according to the equation (4):

$$\text{Arc} = \sqrt{R^2 + \text{pitch}^2}\,\theta \quad (4)$$

In some embodiments, the length Arc may be a predetermined value based on the number of active elements arranged on the flexible sensor strip 200. The processor 120 or remote computing device 250 may calculate the value of pitch using equation (1) by knowing the arc length Arc and manually or wirelessly inputting values for the radius R and parameter θ.

After determining values for the radius R, angle θ, and pitch for each sensor location, the processor may further calculate each sensor's location in three-dimensional space (e.g., axes x, y, and z) using equations (1), (2), and (3). The processor 120 or remote computing device 250 may further calculate the direct distance between the locations of respective sensor elements based on equation (5) below.

$$\text{Distance} = \sqrt{x^2 + y^2 + z^2} \quad (5)$$

In some embodiments, the multi-sensor device 100 may be applied across multiple limbs at the same time (e.g., the subject's finger, wrist, and arm or the subject's foot, ankle, and leg) and the output signals of the sensors 110a-110N used to scan all the limbs at once for a targeted biological structure. In some embodiments, the output signals of the sensors 110a-110N of the multi-sensor device 100 configured in this manner may be used to identify a particular limb amongst the various limbs to which the device is applied for scanning.

In block 340, the processor 120 may provide one or more biometric properties (e.g., blood pressure, heart rate, etc.) determined in block 330 or other types of measurements (i.e., location of an artery, artery identification, etc.). For example, in some embodiments, the processor 120 may provide measurements of one or more biometric properties through an output device, including but not limited to a display or audible component (not shown) of a remote computing device (e.g., 250). In some embodiments, the processor 120 may communicate the one or more determined biometric properties over a wired or wireless communication link via a RF resource 140 and antenna 142 to a remote computing device (e.g., 250) for visual or audible presentation.

Figure 5:
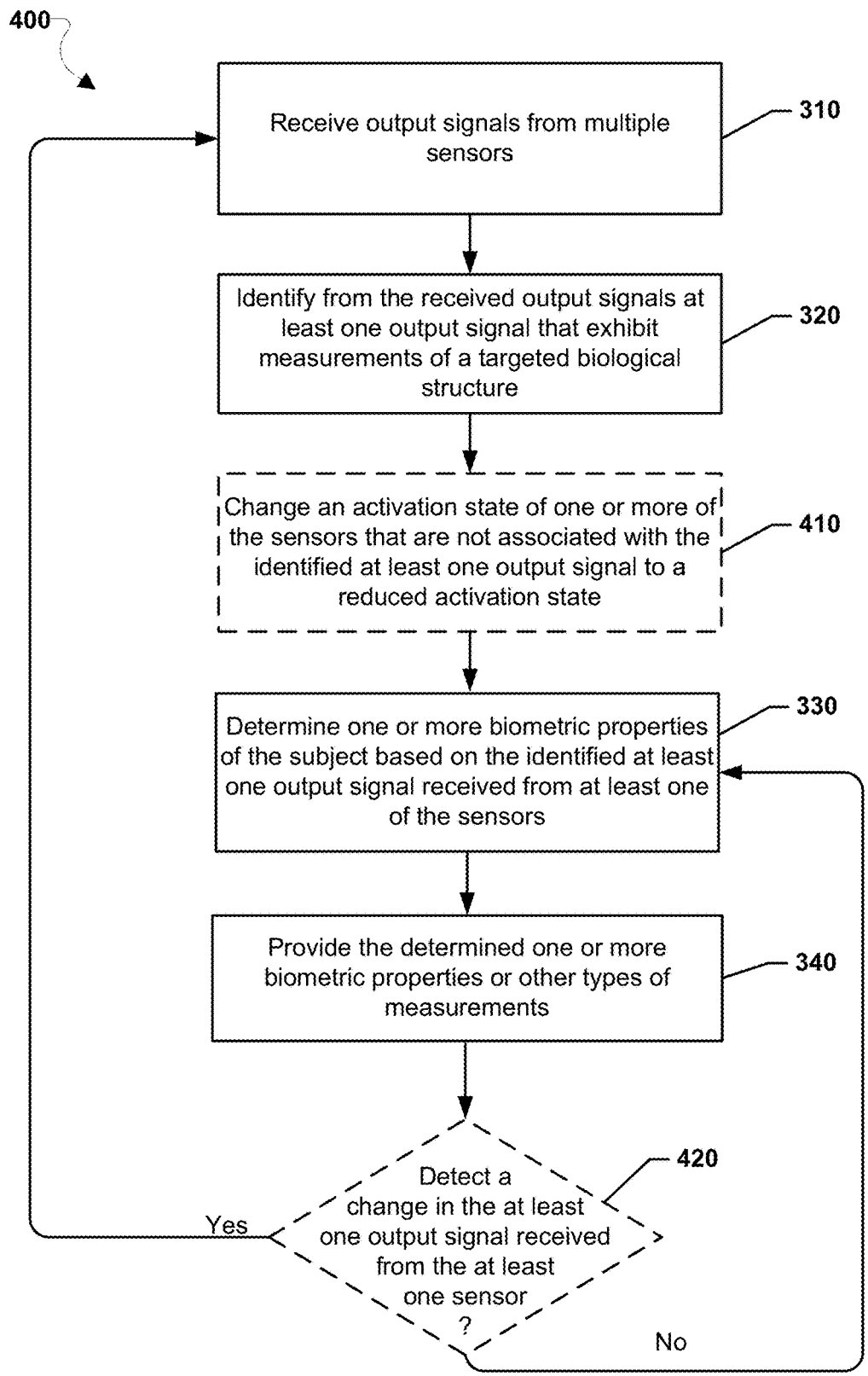
FIG. 5 is a process flow diagram illustrating another method for determining one or more biological properties of a subject using a multi-sensor device according to some embodiments.

FIG. 5 is a process flow diagram illustrating another method 400 for determining one or more biological properties of a subject using a multi-sensor device 100 according to some embodiments. The method 400 may include operations in blocks 310-340 as described with reference to FIG. 3.

In optional block 410, the processor 120 may be configured to change an activate state of one or more of the sensors 110a-110N that are not associated with the output signal identified in block 320 to a reduced activation state. For example, in some embodiments, the processor 120 may deactivate one or more of the sensors that are not exhibiting measurements corresponding to the targeted biological structure in the reduced activation state. In some embodiments, the processor 120 may reduce the rate at which the sensors are activated. For example, the processor may be configured to activate sensors exhibiting measurements that indicate the sensors are not close to a targeted artery every few minutes to perform measurements, and to activate or configure a sensor exhibiting measurements that indicate the sensor is close enough to the targeted artery to obtain reliable measurements to perform measurements frequently, e.g. every second. In this way, the processor 120 may be configured to conserve power and/or reduce energy emitted into the subject (e.g., the electrical signals applied to skin by bio-impedance sensors) while obtaining reliable measurements.

In determination block 420, the processor 120 may determine whether a change is detected in the output signal identified in block 320 received from the at least one of the sensors 110a-110N. For example, the processor may detect that the amplitude of the output signal has weakened or no longer exhibits measurements of the targeted biological structure (e.g., artery). In response to detecting no change in the at least one output signal received from the at least one sensor (i.e., determination block 420="No"), the processor may continue to determine the one or more biometric properties of the subject based on the one or more output signals received from at least one of the sensors identified in block 320.

In response to detecting a change in the at least one output signal received from the at least one sensor (i.e., determination block 420="Yes"), the processor 120 may attempt to identify at least one other output signal that exhibits measurements of the targeted biological structure from a different sensor and determine the one or more biometric properties of the subject based on the identified at least one output signal from at least one different sensor by repeating the operations of blocks 310, 320, 410, and 330. This determination may ensure that the change in the output signal identified in block 420 is not due to movements of the multi-sensor device 100 or the patient causing a misalignment between the device 100 and the measurement location.

Those of skill in the art will appreciate that the foregoing method description and the process flow diagram are provided merely as illustrative examples and are not intended to require or imply that the steps of the various embodiments must be performed in the order presented. The operations in the foregoing embodiment methods may be performed in any order. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope embodiments.

The hardware used to implement the various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

The functions in the various embodiments may be implemented in hardware, software, firmware, or any combination thereof. If implemented in software, the functions may be stored as one or more processor executable instructions or code on a non-transitory computer readable medium or non-transitory processor readable medium. The steps of a method or algorithm disclosed herein may be embodied in a processor-executable software module that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the claims. Various modifications to these embodiments will be readily apparent to those skilled in the art, and the generic principles defined herein may be applied to other embodiments without departing from the scope of the claims. Thus, the claims are not intended to be limited to the embodiments shown herein but are to be accorded the widest scope consistent with the following claims and the principles and novel features disclosed herein.

What is claimed is:

1. A device for determining one or more biometric properties of a subject, comprising;
    a flexible backing;
    a plurality of sensors positioned along the flexible backing; and
    at least one processor coupled to the plurality of sensors, the at least one processor configured to:
    receive output signals from the plurality of sensors;
    identify at least one output signal from the received output signals that exhibits measurements of a targeted biological structure;
    select, from the plurality of sensors, a sensor to deactivate or transition to a low power mode based on identifying the at least one output signal;
    determine the one or more biometric properties of the subject based on the identified at least one output signal;
    deactivate or transition the selected sensor to the low power mode; and
    provide the determined one or more biometric properties.

2. The device of claim 1, wherein to identify the at least one output signal from the received output signals that exhibits measurements of the targeted biological structure, the at least one processor is further configured to:
    compare the received output signals from the plurality of sensors to a reference signal that models the targeted biological structure; and
    identify the at least one output signal based on the comparison.

3. The device of claim 1, wherein the plurality of sensors comprise one or more types of sensors and wherein the at least one processor is further configured to activate the one or more types of sensors to obtain different measurements of the targeted biological structure.

4. The device of claim 3, wherein the one or more types of sensors include optical sensors, bio-impedance sensors, ultrasound imagers, ultrasound sensors, pressure sensors, Peltier sensors, electrocardiogram (ECG) sensors, electromyography (EMG) sensors, electroencephalography (EEG) sensors, ultraviolet (UV) sensors, accelerometers, inertia sensors, or any combination thereof.

5. The device of claim 1, wherein the at least one processor is further configured to change an activation state of one or more of the plurality of sensors that are not associated with the identified at least one output signal to a reduced activation state.

6. The device of claim 3, wherein the at least one processor is configured to activate all of the plurality of sensors simultaneously.

7. The device of claim 3, wherein the at least one processor is configured to activate at least one subset of the plurality of sensors at a similar time.

8. The device of claim 3, wherein the at least one processor is configured to activate the plurality of sensors periodically or quasi-periodically to generate the output signals.

9. The device of claim 1, wherein the at least one processor is further configured to:
   detect a change in the at least one output signal received from at least one sensor of the plurality of sensors;
   identify at least one other output signal that exhibit measurements of the targeted biological structure received from at least one different sensor of the plurality of sensors in response to detecting the change in the at least one output signal; and
   determine the one or more biometric properties of the subject based on the identified at least one output signal received from at least one different sensor.

10. The device of claim 1, wherein the flexible backing is a flexible strip configured to wrap around a subject or a portion of the subject in a helical manner.

11. The device of claim 1 wherein the plurality of sensors are covered with a material to protect the skin.

12. A method for determining one or more biometric properties of a subject using a device, the method comprising:
   receiving, from a plurality of sensors positioned along a flexible backing of the device, output signals;
   identifying, by at least one processor coupled to the plurality of sensors, at least one output signal from the received output signals that exhibits measurements of a targeted biological structure;
   selecting, by the at least one processor, and from the plurality of sensors, a sensor to deactivate or transition to a low power mode based on identifying the at least one output signal;
   determining, by the at least one processor, the one or more biometric properties of the subject based on the identified at least one output signal;
   deactivating or transitioning, by the at least one processor, the selected sensor to the low power mode; and
   providing, by the at least one processor, the determined one or more biometric properties.

13. The method of claim 12, wherein identifying the at least one output signal from the received output signals that exhibits measurements of the targeted biological structure comprises:
   comparing the received output signals from the plurality of sensors to a reference signal that models the targeted biological structure; and
   identifying the at least one output signal based on the comparison.

14. The method of claim 12, wherein the plurality of sensors comprise one or more types of sensors, the method further comprising:
   activating the one or more types of sensors to obtain different measurements of the targeted biological structure.

15. The method of claim 12, wherein receiving the output signals from the plurality of sensors comprises receiving the output signals from optical sensors, bio-impedance sensors, ultrasound imagers, ultrasound sensors, pressure sensors, Peltier sensors, electrocardiogram (ECG) sensors, electromyography (EMG) sensors, electroencephalography (EEG) sensors, ultraviolet (UV) sensors, accelerometers, inertia sensors, or any combination thereof.

16. The method of claim 12, further comprising:
   changing an activation state of one or more of the plurality of sensors that are not associated with the identified at least one output signal to a reduced activation state.

17. The method of claim 14, further comprising activating all of the plurality of sensors simultaneously.

18. The method of claim 14, further comprising activating subsets of the plurality of sensors at a similar time.

19. The method of claim 14, further comprising activating periodically or quasi-periodically the plurality of sensors to generate the output signals.

20. The method of claim 12, further comprising:
   detecting a change in the at least one output signal received from at least one sensor of the plurality of sensors;
   identifying at least one other output signal that exhibits measurements of the targeted biological structure received from at least one different sensor of the plurality of sensors in response to detecting the change in the at least one output signal; and
   determining the one or more biometric properties of the subject based on the identified at least one output signal received from at least one different sensor.

21. The method of claim 12, wherein the flexible backing is a flexible strip configured to wrap around the subject or a portion of the subject in a helical manner.

22. A non-transitory processor-readable storage medium having stored thereon processor executable instructions configured to cause a processor of a multi-sensor device to perform operations comprising:
   receiving, from a plurality of sensors positioned along a flexible backing of the multi-sensor device, output signals;
   identifying at least one output signal from the received output signals that exhibits measurements of a targeted biological structure;
   selecting, from the plurality of sensors, a sensor to deactivate or transition to a low power mode based on identifying the at least one output signal;
   determining the one or more biometric properties of a subject based on the identified at least one output signal;
   deactivating or transitioning the selected sensor to the low power mode; and
   providing the determined one or more biometric properties.

23. The non-transitory processor-readable storage medium of claim 22, wherein to identify the at least one output signal from the received output signals that exhibit measurements of the targeted biological structure, and wherein the stored processor executable instructions are configured to cause the processor to perform operations further comprising:
   comparing the received output signals from the plurality of sensors to a reference signal that models the targeted biological structure; and
   identifying the at least one output signal based on the comparison.

24. The non-transitory processor-readable storage medium of claim 22, wherein the plurality of sensors comprise one or more types of sensors, and wherein the stored processor executable instructions are configured to cause the processor to perform operations further comprising:
   activating the one or more types of sensors to obtain different measurements of the targeted biological structure.

25. The non-transitory processor-readable storage medium of claim 22, wherein to, the stored processor executable instructions are configured to cause the processor to perform operations such that receiving the output signals from the plurality of sensors comprises receiving the output signals from optical sensors, bio-impedance sensors, ultrasound imagers, ultrasound sensors, pressure sensors, Peltier sensors, electrocardiogram (ECG) sensors, electromyography (EMG) sensors, electroencephalography (EEG) sensors, ultraviolet (UV) sensors, accelerometers, inertia sensors, or any combination thereof.

26. The non-transitory processor-readable storage medium of claim 22, wherein the stored processor executable instructions are configured to cause the processor to perform operations further comprising:
changing an activation state of one or more of the plurality of sensors that are not associated with the identified at least one output signal to a reduced activation state.

27. The non-transitory processor-readable storage medium of claim 22, wherein the stored processor executable instructions are configured to cause the processor to perform operations further comprising:
detecting a change in the at least one output signal received from at least one sensor of the plurality of sensors;
identifying at least one other output signal that exhibits measurements of the targeted biological structure received from at least one different sensor of the plurality of sensors in response to detecting the change in the at least one output signal; and
determining the one or more biometric properties of the subject based on the identified at least one output signal received from at least one different sensor.

28. The non-transitory processor-readable storage medium of claim 22, wherein the flexible backing is a flexible strip configured to wrap around the subject or a portion of the subject in a helical manner.

29. A device for determining one or more biological properties of a subject, comprising:
a flexible backing;
a plurality of sensors positioned along the flexible backing;
means for receiving output signals from the plurality of sensors;
means for identifying at least one output signal from the received output signals that exhibit measurements of a targeted biological structure;
means for selecting, from the plurality of sensors, a sensor to deactivate or transition to a low power mode based on the identification of the at least one output signal;
means for determining the one or more biometric properties of the subject based on the identified at least one output signal;
means for deactivating or transitioning the selected sensor to the low power mode; and
means for providing the determined one or more biometric properties.

30. The device of claim 1, wherein the at least one processor is configured to select, from the plurality of sensors, the sensor to deactivate or transition to a low power mode based on determining that the sensor not providing the identified at least one output signal.

31. The device of claim 1, wherein the at least one processor is configured to select, from the plurality of sensors, the sensor to deactivate or transition to a low power mode based on determining that an output from the sensor does not exhibit measurements of the targeted biological structure.

32. The device of claim 9, wherein the at least one processor is further configured to deactivate or transition the at least one sensor of the plurality of sensors to the low power mode based on determining that the changed at least one output signal does not exhibit measurements of the targeted biological structure.

33. The device of claim 1, wherein the plurality of sensors are configured to perform same type of measurements of the targeted biological structure.

* * * * *